US011598760B2

(12) United States Patent
Masri et al.

(10) Patent No.: US 11,598,760 B2
(45) Date of Patent: Mar. 7, 2023

(54) GEOLOGIC CORE INSPECTION TABLE

(71) Applicant: Saudi Arabian Oil Company, Dhahran (SA)

(72) Inventors: Abdul Hafiz O. Masri, Dhahran Hills (SA); Mokhles M. Mezghani, Dhahran (SA); Mustafa A. Al Ibrahim, Safwa (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 520 days.

(21) Appl. No.: 16/750,473

(22) Filed: Jan. 23, 2020

(65) Prior Publication Data

US 2021/0231631 A1    Jul. 29, 2021

(51) Int. Cl.

| G01N 33/24 | (2006.01) |
|---|---|
| A47B 9/10 | (2006.01) |
| A47B 9/20 | (2006.01) |
| A47B 13/00 | (2006.01) |
| A47B 37/00 | (2006.01) |
| B60B 33/00 | (2006.01) |
| G02B 21/24 | (2006.01) |

(52) U.S. Cl.
CPC .............. G01N 33/24 (2013.01); A47B 9/10 (2013.01); A47B 9/20 (2013.01); A47B 13/003 (2013.01); A47B 37/00 (2013.01); B60B 33/0078 (2013.01); A47B 2037/005 (2013.01); A47B 2200/0051 (2013.01); A47B 2200/0062 (2013.01); G02B 21/24 (2013.01)

(58) Field of Classification Search
CPC .................................. G01N 1/00; G01N 1/28
USPC ...... 73/864.91; 108/50.01, 50.02, 147, 27, 7
See application file for complete search history.

(56) References Cited

U.S. PATENT DOCUMENTS

| 1,927,598 | A | * | 9/1933 | Schlichter | ................. | B66F 7/14 |
|---|---|---|---|---|---|---|
| | | | | | | 104/32.1 |
| 3,034,843 | A | * | 5/1962 | Moon | ..................... | F25D 15/00 |
| | | | | | | 312/277 |
| 3,080,835 | A | * | 3/1963 | Guglielmi | ................ | A47B 9/10 |
| | | | | | | 108/147 |
| 3,217,672 | A | | 11/1965 | Haughey | | |

(Continued)

FOREIGN PATENT DOCUMENTS

| AU | 631116 B2 | 11/1992 |
|---|---|---|
| AU | 2013204793 B2 | 1/2016 |

(Continued)

OTHER PUBLICATIONS

International Preliminary Examining Authority Written Opinion for PCT/IB2020/051425, 12 pages (dated May 11, 2021).

(Continued)

*Primary Examiner* — Jose V Chen
(74) *Attorney, Agent, or Firm* — Osha Bergman Watanabe & Burton LLP (57) ABSTRACT

A geologic core inspection table includes at least two legs, each including an extending portion for increasing the effective length of each leg, the extending portion at least partially concentrically disposed within or about the leg from which it extends; and a tabletop disposed above and coupled to the legs. The tabletop includes a top surface for receiving a core sample tray. At least one leg may be extended to a different height than at least one other leg.

25 Claims, 4 Drawing Sheets

(56) References Cited

U.S. PATENT DOCUMENTS

| | | | |
|---|---|---|---|
| 3,652,103 A | | 3/1972 | Higgs |
| 3,782,582 A | | 1/1974 | Lybbert et al. |
| 3,786,932 A | | 1/1974 | Smith |
| 4,440,096 A | * | 4/1984 | Rice .......................... A47B 9/04 108/4 |
| 4,590,866 A | | 5/1986 | Schairbaum |
| 4,754,713 A | * | 7/1988 | Chatenay epouse Compagnone ............ A63J 1/00 108/147 |
| 4,927,022 A | * | 5/1990 | Wilson ................... B65D 85/20 206/443 |
| 5,088,421 A | * | 2/1992 | Beckstead ................ A47B 9/12 248/406.1 |
| 5,323,695 A | * | 6/1994 | Borgman ................. A47B 9/00 108/147 |
| 5,499,697 A | | 3/1996 | Trimble et al. |
| 5,636,394 A | * | 6/1997 | Bartley ................ A47C 19/045 108/147 |
| 5,730,408 A | | 3/1998 | McAllister et al. |
| 6,237,725 B1 | | 5/2001 | Otterson et al. |
| 6,474,246 B2 | * | 11/2002 | Hsu .......................... A47B 9/04 108/147 |
| 6,644,216 B1 | * | 11/2003 | Cole ........................ A47B 9/16 108/1 |
| 6,960,098 B1 | * | 11/2005 | Tseng ..................... H01R 13/73 439/502 |
| 7,062,958 B2 | | 6/2006 | Diakonov et al. |
| 7,270,062 B1 | * | 9/2007 | Larson .................... A47B 9/10 108/150 |
| 7,395,902 B2 | | 7/2008 | D'Arca et al. |
| 8,112,836 B2 | * | 2/2012 | Tesar ..................... A61G 7/005 108/4 |
| 8,490,555 B1 | | 7/2013 | Agee |
| 9,826,825 B1 | | 11/2017 | Jones et al. |
| 10,260,336 B2 | | 4/2019 | Smith |
| 11,197,541 B1 | * | 12/2021 | Fullerton ............. A47B 83/001 |
| 2002/0043604 A1 | | 4/2002 | Cooper et al. |
| 2002/0084389 A1 | * | 7/2002 | Larson .................... A47B 21/00 248/371 |
| 2004/0135045 A1 | | 7/2004 | Larson |
| 2005/0023787 A1 | | 2/2005 | Haynes |
| 2007/0068429 A1 | * | 3/2007 | Frazier ................. A47B 13/088 108/147 |
| 2010/0018886 A1 | | 1/2010 | Wilson |
| 2011/0168064 A1 | * | 7/2011 | Jahnsen ............... A47B 13/021 108/147 |
| 2015/0320213 A1 | * | 11/2015 | Sorrell ..................... A47B 9/04 108/147.19 |
| 2016/0095426 A1 | * | 4/2016 | Tempas .................... A47B 9/02 108/147 |
| 2018/0251333 A1 | | 9/2018 | Knierim et al. |

FOREIGN PATENT DOCUMENTS

| | | |
|---|---|---|
| AU | 2017225152 B2 | 10/2018 |
| JP | 2017166837 A | 9/2017 |
| WO | WO-2002/024028 A1 | 3/2002 |
| WO | WO-2014/170826 A2 | 10/2014 |
| WO | WO-2021/148847 A1 | 7/2021 |

OTHER PUBLICATIONS

International Search Report for PCT/IB2020/051425, 5 pages (dated Aug. 7, 2020).
Wilson, G., Geological Work Bench (May 2019), <https://41d8c69f-fcbd-4e96-bc95-0669d8e35526.filesusr.com/ugd/6b1c4d_0236289a96bf4e0c90facb322a1327ec.pdf>. Retrieved Jul. 29, 2020.
Written Opinion for PCT/IB2020/051425, 10 pages (dated Aug. 7, 2020).

* cited by examiner

GEOLOGIC CORE INSPECTION TABLE

FIELD

The subject matter described herein relates to apparatuses, systems, and methods for inspecting geologic core samples.

BACKGROUND

Current oil and gas exploration enterprises commonly use geologic cores, long cylindrical rock samples obtained from the subsurface of a formation, as essential data sources in geoscientific studies. Core samples may commonly undergo several activities which raise two main concerns: minimizing the damage to the core samples (which often results in attempts to minimize handling), as well as improving the safety of the technicians and material handlers handling the core samples. Core samples are studied by geoscientists. Therefore, core sample handling systems must cater to the aforementioned activities and concerns. Core sample trays may be designed to accommodate a total weight of 75 kg (165 lbs.). Repeated-use type injuries to the back, neck, arms and other body parts may result from the strains of continually moving core samples and slabs from one table to the next. In addition, accident-type injuries may result from core samples falling from tables or off trays, which may increasingly result from cores and slabs being transferred from one inspection area to another, or to one or more storage areas. Geoscientists inspecting and studying the cores often find the viewing areas unsuitable (too high, too low, etc.) In addition, space for housing or storing needed equipment may be limited in the core sample viewing area.

SUMMARY OF THE INVENTION

The present disclosed embodiments include apparatuses, systems, and methods for enabling the storage, examination, inspection, and movement of geologic core samples using tables with adjustable height, mobility features such as wheels, as well as safety features such as moveable side stoppers, to prevent core sample trays from sliding or falling. The present disclosed embodiments include a modular geologic core preparation and examination table, which may be customized with features specifically designed to accommodate the needed safety, mobility, and versatility of usage. The system may include features for adjusting the height and tilt of the table, accommodating different core tray configurations, as well as moving and storing both needed equipment, as well as the core samples and slabs themselves. The system may include core trays that are designed specifically to handle slabbed geologic cores. The table may also include features for interconnecting with other tables, if extra examination or storage space is needed.

In one aspect of the present invention, a geologic core inspection table includes: at least two legs, each leg including an extending portion for increasing the effective length of each leg, the extending portion at least partially concentrically disposed within or around the leg from which it extends; and a tabletop disposed above and coupled to the at least two legs, the tabletop including a top surface for receiving a core sample tray, where at least one leg is extended to a different height than at least one other leg.

In some embodiments, each extending portion is telescopically coupled to the respective leg from which it extends.

In some embodiments, the top surface for receiving a core sample tray is oriented at an angle from about 10 degrees to about 30 degrees relative to a horizontal direction.

In some embodiments, the table includes a bearing assembly coupling at least one of the legs to a bottom surface of the tabletop.

In some embodiments, the bearing assembly includes a T-coupling.

In some embodiments, the table includes a retractable movable tray coupled to a bottom surface of the tabletop.

In some embodiments, the table includes a control console disposed on the tabletop, the control console controlling the height of the tabletop.

In some embodiments, the table includes a shelf coupled to the at least two legs and disposed beneath the tabletop.

In some embodiments, the table includes a hydraulic system including: a pneumatic cylinder disposed within a hollow interior of a leg; hydraulic fluid disposed within the pneumatic cylinder; and a hydraulic fluid pressure source fluidly connected to the hydraulic fluid.

In some embodiments, the table includes a retractable movable tray coupled to a bottom surface of the tabletop; a control console disposed on the tabletop; and a shelf coupled to the legs and disposed beneath the tabletop.

In some embodiments, the table includes wheels coupled to the legs; a brake coupled to one of the wheels; and a manual brake release coupled to the brake, where the wheels include a castor, and where each extending portion is telescopically coupled to the leg from which it extends.

In another aspect of the present invention, a geologic core inspection table includes: at least three legs, each leg comprising a wheel coupled thereto, the wheels allowing movement of the table in both a lateral direction and a longitudinal direction; and a tabletop disposed above and coupled to the at least three legs, the tabletop including a top surface for receiving a core sample tray, where at least one leg is extended to a different height than at least one other leg.

In some embodiments, the table includes a brake coupled to the wheel, the brake including a spring for engaging the brake on the wheel.

In some embodiments, the table includes a manual brake release coupled to the brake.

In some embodiments, the wheel includes a castor.

In another aspect of the present invention, a geologic core inspection table system includes: a core tray for holding core samples, the core tray comprising two or more grooves disposed therein, each groove of the two or more grooves extending longitudinally for receiving a core sample; and a geologic core inspection table including: at least two legs; and a tabletop disposed above and coupled to the legs, the tabletop including a surface for receiving the core tray, where at least one leg is extended to a different height than at least one other leg.

In some embodiments, the core tray has a length from about 100 cm to about 120 cm.

In some embodiments, the system includes a toblerone insert disposed within a groove.

In some embodiments, the toblerone insert and the core tray each include at least one embedded handle.

In some embodiments, the system includes: rollers disposed on the tabletop; and a cover covering the rollers; where the geologic core inspection table further includes a side stopper for preventing core samples from falling off of the geologic core inspection table.

In some embodiments, at least one of the core tray and the geologic core inspection table is composed of austenitic steel, carbon steel, galvanized stainless steel, titanium, or a combination thereof.

In some embodiments the geologic core inspection table includes at least four legs.

In some embodiments, at least two legs include a bottom portion extending parallel to the ground.

In some embodiments, at least two legs comprising an upside-down "T" shape or an "I" shape.

In some embodiments, the top surface for receiving a core sample tray is oriented at an angle from about 5 degrees to about 35 degrees relative to a surface on which the geologic core inspection table is resting.

In some embodiments, the system includes a control console disposed on the tabletop, the control console controlling the height of the tabletop relative to a surface on which the geologic core inspection table is resting.

Throughout the description, where an apparatus, systems or compositions are described as having, including, or comprising specific components, or where methods are described as having, including, or comprising specific steps, it is contemplated that, additionally, there are systems, apparatuses or compositions of the present invention that consist essentially of, or consist of, the recited components, and that there are methods according to the present invention that consist essentially of, or consist of, the recited processing steps.

It should be understood that the order of steps or order for performing certain action is immaterial as long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the present claims. The Background section is presented for purposes of clarity and is not meant as a description of prior art with respect to any claim.

BRIEF DESCRIPTION OF THE DRAWINGS

A full and enabling disclosure of the present disclosed embodiments, including the best mode thereof, directed to one of ordinary skill in the art, is set forth in the specification, which makes reference to the appended figures, in which.

DESCRIPTION OF CERTAIN ASPECTS OF THE INVENTION

Reference will now be made in detail to the present disclosed embodiments, one or more examples of which are illustrated in the accompanying drawings. The detailed description uses numerical and/or letter designations to refer to features in the drawings. Like or similar designations in the drawings and description have been used to refer to like or similar parts of the present embodiments.

Geologic Core Inspection Table

Figure 1:
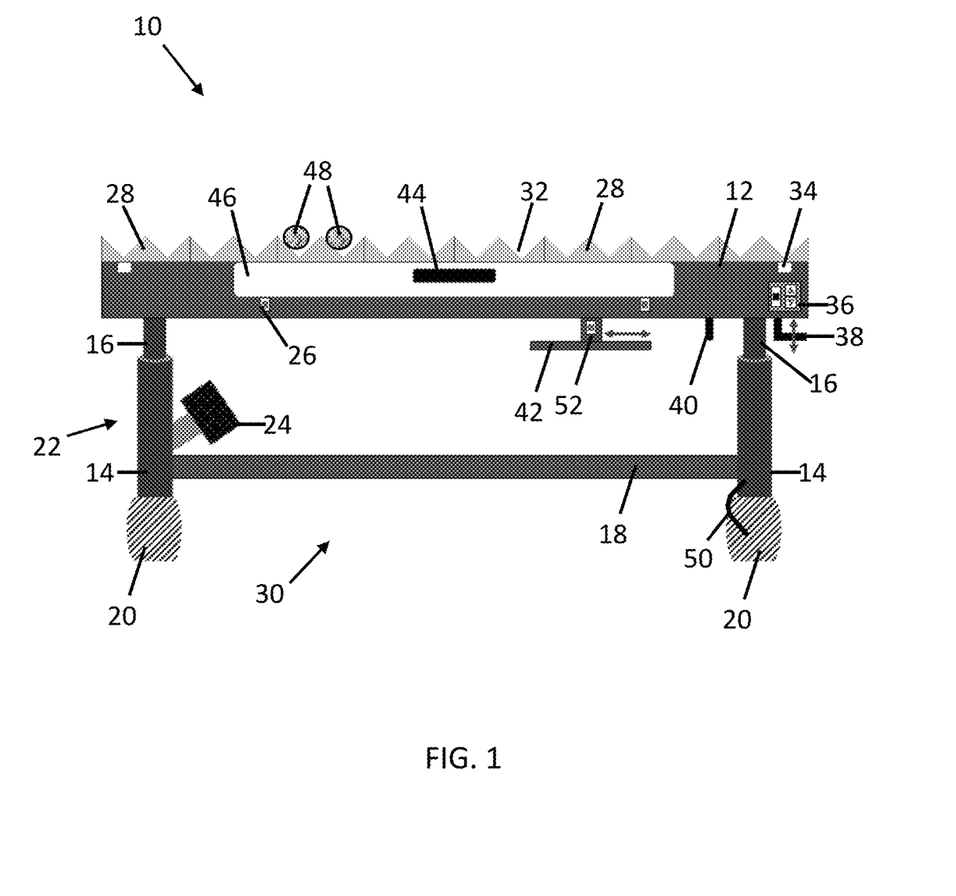
FIG. 1 illustrates a front view of a core inspection table, according to aspects of the present embodiments.

FIG. 1 illustrates a front view of a table system 10, according to the present disclosed embodiments, including a geologic core inspection table 30 and one or more core trays 28. The inspection table 30 may include one or more legs 14, which each may include one or more extending portions 16 for raising or lowering the height of the inspection table 30. Each extending portion 16 may be concentrically disposed within the respective leg 14 from which it extends. In other embodiments, each extending portion 16 may be concentrically disposed around the respective leg 14 from which it extends. In a retracted position, each extending portion 16 may be fully concentrically disposed within the respective leg 14 from which it extends. In an extended position, each extending portion 16 may be only partially concentrically disposed within the respective leg 14 from which it extends. As such, each extending portion 16 is telescopically coupled to the respective leg 14 from which it extends. In the embodiment of FIG. 1, the inspection table 30 may include four legs 14 (that is, the two legs 14 that are illustrated, as well as two more legs 14 that are not visible, behind the two legs 14 that are visible in FIG. 1). The inspection table 30 may also include a tabletop 12 on which core samples and trays may be placed, as well as one or more shelves 18 extending horizontally between the four legs 14, and providing storage space for core trays 28, core samples 48, instrumentation, temporary storage of materials, toblerone inserts (shown in FIGS. 10-12), and other equipment. The shelf 18 may be located so as to provide enough room thereunder to accommodate the feet of the geoscientist, technician, material handler, or operator (for example, about twenty (20) cm clearance with the floor, or from about 15 cm to about 25 cm clearance with the floor, or from about 10 cm to about 30 cm clearance with the floor. The inspection table 30 may also include one or more wheels 20 disposed at the bottom of each leg 14. The one or more wheels 20 may include castors (or casters, such as ball castors, spherical ball castors, swivel castors, shepherd castors, and other types of casters) as well as other types of wheels or rolling mechanisms allowing both lateral (or width-wise) movement as well as longitudinal (or length-wise) movement.

Referring still to FIG. 1, the inspection table 30 may also include at least one brake release 38 which may be used to release one or more brakes 50 on the wheels 20 such that the inspection table 30 may be moved. For example, the at least one brake release 38 may be coupled via a linkage, cable or other coupling to at least one brake 50 disposed on at least one of the wheels 20. The at least one brake may be spring-loaded such that in a default position, the at least one brake 50 is engaged on the wheel (thereby preventing the table from rolling or moving). When the at least one brake release 38 is manually squeezed by an operator, the at least one brake 50 may disengage the one or more wheels 20. The at least one brake release 38 may also act as a handle allowing the operator to move, steer, and maneuver the inspection table 30 as needed, while simultaneously holding the at least one brake release 38, enabling movement of the inspection table 30. The inspection table 30 may also include one or more automatic braking disengagement handles (or levers) 40 that may be used to temporarily or permanently disengage the brake 50 from the wheel 20. In one embodiment, multiple inspection tables 30 may be coupled together (for example, via one or more rigid attachments disposed underneath tabletop 12) such that the multiple inspection tables 30 may be moved simultaneously by a single operator. When multiple inspection tables 30 are coupled, the automatic braking disengagement handle 40 may be used to disengage the brake 50 on one table, allowing the operator to use the brake release 38 of the other table as a braking mechanism for both tables (and thereby requiring the operator to squeeze only a single brake release 38 in order to move or maneuver multiple inspection tables 30 simultaneously).

Still referring to FIG. 1, the inspection table 30 may include a retractable movable tray 42, which may be used for housing laptops, notebooks, pens, hand lenses, acid bottles, grain size charts, rulers, papers, instrumentation, and other equipment. The retractable moveable tray 42 may also include one or more elongated grooves specifically designed for holding one or more pens and preventing them from rolling. The retractable moveable tray 42 may slide longitudinally the full length of the inspection table 30 (for example, using a wheel and runner or tracks attached to the underside of the tabletop 12), thereby aiding in the inspection in different areas of the inspection table 30. The retractable moveable tray 42 may also be retracted (for example, using a hinge that locks into place) to a storage position under the tabletop 12 when not in use, thereby enhancing the ease in which both the inspection table 30 may be maneuvered, as well as the ease with which operators may move around the inspection table 30. The retractable moveable tray 42 may also include an electrical output 52, for plugging in laptops, microscopes, and other equipment, the electrical output 52 being powered by an electrical wire (not shown) under the table that may be wound around a spring-loaded spool, allowing the wire to wind and unwind around the spool in order to track the movement of the retractable moveable tray 42. The electrical wire (not shown) may be powered via a table power supply (not shown) which in turn may be powered by plugging in the table (for example, into a 110V-240V wall outlet or power strip). One or more electrical outlets 26 may also be disposed directly in the inspection table 30 (for example, on the tabletop 12), in addition to or instead of the electrical output 52 in the retractable moveable tray 42. In one embodiment, two electrical outlets may be disposed in each elongated side (or length) of the inspection table 30. The one or more electrical outlets 26 may be used to power different devices such as laptops or small microscopes. One or more switches for controlling each electrical output 26 may be disposed within (and coupled to) the control console 36.

Referring still to FIG. 1, the inspection table 30 may include a hydraulic system 22, at least partially disposed within one table leg 14. The hydraulic system 22 may include at least one extending portion 16 of the table leg 14 for extending (or retracting) each table leg 14, thereby raising or lowering the height of the table 30. The hydraulic system 22 may also include hydraulic fluid (not shown) disposed within the hollow interior of one or more table legs 14, the hollow interior acting as a pneumatic cylinder. The hydraulic system 22 may also include one or more pumps or compressors (not shown) for pressurizing the hydraulic fluid. In addition, one or more control consoles 36 may be operatively coupled to the hydraulic system 22 such that an operator may press an up button or down button as needed to raise and lower the tabletop 12. The hydraulic system 22 may also include a power source (or power supply) such as a 220V power supply (for example, from plugging the table into the wall) which may be used to power the one or more pumps or compressors. The hydraulic system 22 may also include a manual hydraulic system controller 24 which may be used to both pressurize and release the hydraulics when the inspection table 30 is not plugged in. For example, the manual hydraulic system controller 24 may act as a hydraulic pressure relief mechanism when lowering the tabletop 12 is desired, in situations where electrical power sources are unavailable. Similarly, the manual hydraulic system controller 24 may be actuated back and forth to jack or ratchet the tabletop 12 upwards (via the hydraulic fluid within the one or more legs, or via one or more crank handles disposed on the manual hydraulic system controller 24, or elsewhere within the hydraulic system 22) when a higher position of the tabletop 12 is desired, again, in circumstances where electrical power sources are unavailable. In the illustration of FIG. 1, the inspection table 30 includes a hydraulic system 22 only on the left leg 14. In other embodiments, each leg 14 may include a separate hydraulic system 22, or interconnected components of a single hydraulic system 22. For example, in one or more embodiments, the tabletop 12, the shelf 18, or both the tabletop 12 and the shelf 18 may include one or more fluid passageways to fluidly connect the pneumatic cylinders within multiple legs 14 of the inspection table 30. In other embodiments, an electric motor (which may include one or more gears, linkages, or other actuators) may be used to raise and lower the tabletop 12, rather than a hydraulic system 22.

Still referring to FIG. 1, the inspection table system 10 may include one or more core trays 28 disposed on the tabletop 12, on the shelf 18, or alternatively in another location. Each core 48 may have a diameter from about thirty (30) millimeters to about ninety (90) millimeters, or from about seventy-six (76) millimeters (3 inches) to about one hundred (100) millimeters (4 inches). As such, each core tray 28 may have anywhere from two (2) to about six (6) slots 32 or "runs" for holding core samples 48, depending on the outer diameter of each core sample 48. Each slot 32 may include a length of about one (1) meter, or from about ninety (90) cm to about one-hundred and ten (110) cm, or from about eight (80) centimeters to about one-hundred and twenty (120) centimeters, or from about eight-five (85) centimeters to about one-hundred and five (105) centimeters, or from about ninety-one and a half (91.5) centimeters to about one-hundred (100) centimeters. The core trays 28 may include angled slots 32 in which one or more cores 48 may rest. In other embodiments, each core tray 28 may include rounded slots (not shown) such that the curvature of each rounded slot approximately matches the curvature of the outer diameter or surface of each core sample 48.

Referring still to FIG. 1, the inspection table 30 may include a side stopper 46 that may be pulled vertically upward from the side of the tabletop 12 to provide a barrier preventing the core tray 28 and core sample 48 from sliding off the inspection table 30. The side stopper 46 may include one or more handles 44 disposed within it, thereby allowing an operator to easily slide the side stopper 46 up and down. The inspection table 30 may also include one or more locks 34 for securing the core trays 28 onto the inspection table 30 once they have been placed on the tabletop 12. The lock 34 may include a clip that engages one or more lips, holes, tabs, tangs, grooves, or other potential locking features of each of the core trays 28 and tabletop 12. In another embodiment, one end of each lock 34 may be permanently fixed to the inspection table 30 in the vicinity of the tabletop 12, while the other end of each lock may engage at least one feature of one or more core trays 28.

Still referring to FIG. 1, the length and width of the inspection table 30 may accommodate the same number of core trays 28. For example, in one embodiment, the width of the inspection table 30 may be one-hundred (100) cm, while the length of the inspection table 30 may be three-hundred (300) cm, which would accommodate twelve (12) core trays 28 each including a width of twenty-five (25) cm, and a length of one-hundred (100) cm. In another embodiment, the width of the inspection table 30 may be one-hundred (100) cm, while the length of the inspection table 30 may be two-hundred (200) cm, which would accommodate eight (8) core trays 28 each including a width of twenty-five (25) cm, and a length of one-hundred (100) cm. In the first example (that is, an inspection table with a length of three-hundred (300) cm), the twelve (12) core trays 28 may each be laid side-by-side, oriented in the same direction, or may be arranged in three (3) 100 cm×100 cm groups, each group being arranged widthwise, lengthwise, or a combination thereof.

Referring still to FIG. 1, each of the tabletop 12 and the shelf 18 must be sturdy enough to accommodate several hundred kilograms. In operation, the expected loading of the inspection table 30 may be on the order of from about 500 kg to about 750 kg. However, higher loads are also possible. For example, if twelve (12) filled core trays 28 each weighing 50 kg are placed on each of the shelf 18 and the tabletop 12, the inspection table may include 600 kg loaded on the tabletop 12 and a total loading of 1200 kg. As such, a two-inch thick shelf 18 or tabletop 12 (in one embodiment comprised of at least one of stainless steel, austenitic steel, carbon steel, galvanized stainless steel, titanium, or other suitable materials) may be used, along with several support members distributing loading from the shelf 18 or tabletop 12 to each of the legs 14, in order to ensure the inspection table 30 is sturdy and robust enough to handle the loading. Similarly, the legs 14 and extending portions 16, wheels 20 (or casters), and other components of the inspection table 30 must all be robust enough to accommodate the expected loading.

In operation, the inspection table 30 may include wheels 20 that are automatically braked (for example, in one embodiment, via a spring-loaded locking mechanism 50) for safety purposes. When one or more inspection tables 30 need to be moved, the brake release 38 may be pressed or squeezed by the operator, technician, material handler, or geoscientists, while the inspection table 30 is simultaneously maneuvered. The brake release 38 may be located underneath the tabletop 12 at one of the width ends, proximate at least one leg 14 or the tabletop 12, to aid in maneuvering the inspection table 30. The braking system may engage one (1), two (2), three (3), or all four (4) of the wheels 20 (that is, the braking system does not need to be connected to all four wheels 20).

Figure 2:
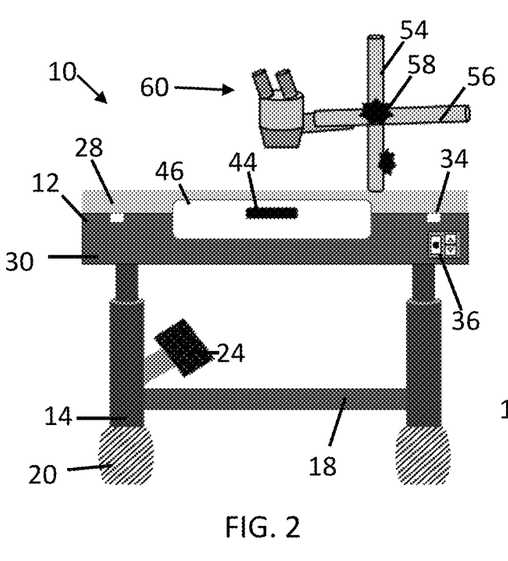
FIG. 2 illustrates a side view of a core inspection table, according to aspects of the present embodiments.

FIG. 2 illustrates a side view of the table system 10 including the inspection table 30, one or more core trays 28, one or more legs 14, one or more wheels 20, the tabletop 12, the control console 36, one or more locks 34, a side stopper 46, a handle 44, and the shelf 18. In the embodiment of FIG. 2, the inspection table 30 includes both the control console 36 as well as a side stopper 46 on the width side of the inspection table 30, which may be instead of, or in addition to the corresponding elements illustrated on the length side of the inspection table 30 in FIG. 1. The inspection table 30 may also include an adjustable microscope 60 mounted to the tabletop 12 including one or more vertical arms 54, and one or more horizontal arms 56, as well as one or more adjusting knobs 58 for adjusting the position of the microscope 60 such that a technician or geoscientist can bring the adjustable microscope 60 close to the core samples (shown in FIG. 1) without having to move the core samples. The adjustable microscope 60 may also include (or be mounted to) longitudinal runners or arms (not shown) for moving the adjustable microscope 60 along a length of the inspection table 30. The adjustable microscope 60 may also include one or more cameras (not shown), for taking magnified pictures of the one or more core samples, as well as a communication connection to one or more networks or electronic computing devices (such as a laptop, smart phone, tablet, or desktop computer) for uploading and downloading images of the core samples 48 from the adjustable microscope 60 or camera (not shown).

Referring still to FIG. 2, in other embodiments, the table 30 may include two (2) or more legs 14, each leg 14 being in the shape of an upside-down "T" including a bottom portion that extends parallel to the floor, thereby preventing the table 30 from tipping over. In other embodiments, the table may include two (2) or more legs 14, each leg 14 including an "I" shape with both a bottom portion that extends parallel to the floor, as well as a top portion that is coupled to a bottom surface of the table 30, and extends parallel to the table 30.

Figure 3:
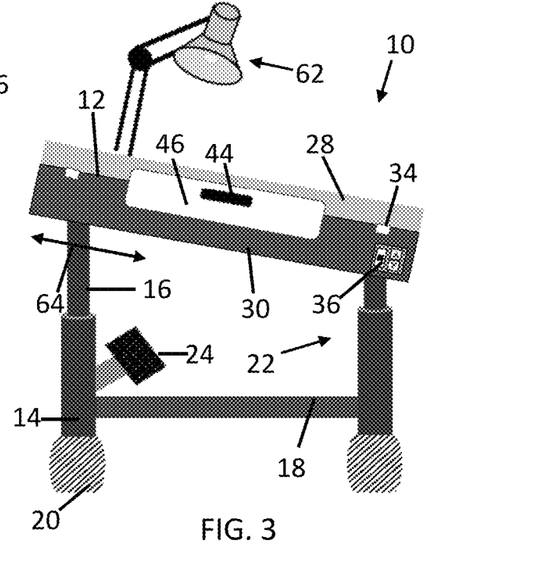
FIG. 3 illustrates a side view of a core inspection table, according to aspects of the present embodiments.

FIG. 3 illustrates a side view of the table system 10 including the inspection table 30, one or more core trays 28, one or more legs 14, one or more wheels 20, the tabletop 12, the control console 36, one or more locks 34, a side stopper 46, a handle 44, and the shelf 18. In the embodiment of FIG. 3, the inspection table 30 includes an extended portion 16 that is more fully extended in the rear two legs 14 (left side of FIG. 3) than in the front two legs (right side of FIG. 3). In the position illustrated in FIG. 3, the inspection table 30 provides an arrangement (or table setup) that makes it easier for a technician, inspector, or geoscientist to view the core samples 48 (shown in FIG. 1) especially the core samples 48 that are at the rear of the table (that is, on the left side of FIG. 3). By elevating the rear of the inspection table 30, the far side of the table is brought closer to the technician, inspector, or geoscientist standing at the front of the table (right side of FIG. 3), thereby alleviating the technician, inspector, or geoscientist from having to bend over the inspection table 30 in order to view the core samples 48 at the far side of the inspection table 30. In the embodiment of FIG. 3, the hydraulic system 22 raises the rear of the inspection table 30, while the front of the inspection table 30 remains in a lower position. In the embodiment of FIG. 3, the inspection table 30 may also include one or more inspection lamps 62, providing directed light onto one or more core samples of interest while inspection activities are being carried out. The inspection lamp(s) 62 may be mounted to the tabletop 12 and may include one or more linkages and rotatable connections for adjusting the position of the inspection lamp 62 as desired. As the rear of the inspection table 30 is being raised (while the front of the inspection table 30 remains in a lower position), the location of the connection between the extending portion 16 and the bottom of the tabletop 12 may translate along a lateral axis 64 (pointing from the back of the inspection table 30 to the front and vice versa). In one or more embodiments, the tabletop 12 of the inspection table 30 may be oriented (relative to a horizontal direction) at an angle of about 20 degrees, or from about 15 degrees to about 25 degrees, or from about 10 degrees to about 30 degrees, or from about 5 degrees to about 35 degrees, or from about zero (0) degrees to about 40 degrees, or at an angle up to about 45 degrees. The horizontal direction may be parallel to the ground a floor, or another surface on which the table 30 is sitting or standing. As such, the tabletop 12 may be oriented at an angle of about 5 degrees to about 35 degrees (for example) relative to the floor or surface on which the table 30 is resting, sitting, or standing.

Figure 4:
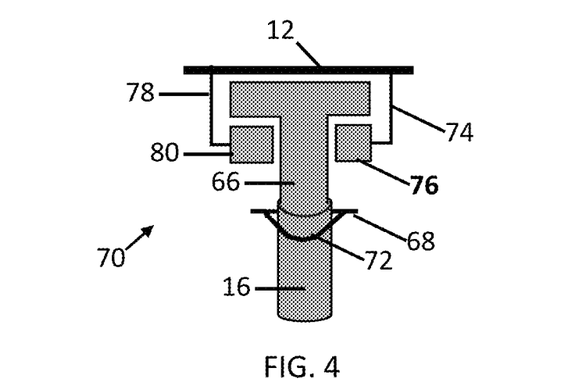
FIG. 4 illustrates a front view of a bearing assembly, according to aspects of the present embodiments.

FIG. 4 illustrates a front view of a bearing assembly 70 that may be used to make the connection between each leg 14 and the tabletop 12. The bearing assembly 70 may include a T-coupling 66 rotatably coupled to the extending portion 16 of the leg via one or more pins 68. The pin 68 may be disposed through both the T-coupling 66 and the extending portion 16 coupling the T-coupling 66 and the extending portion 16 and allowing them to rotate about the pin 68. The pin 68 may be secured via one or more retainers 72 such that the pin 68 does not become separated from either the T-coupling 66 or the extending portion 16. A first coupling 74 may connect a first runner 76 along one side of the T-coupling 66 such that a top portion of the first runner 76 interfaces with a first bottom portion of the T-coupling 66. Similarly, a second coupling 78 may connect a second runner 80 along a second side of the T-coupling 66 such that a top portion of the second runner 76 interfaces with a second bottom portion of the T-coupling 66.

Still referring to FIG. 4, each of the first and second couplings 74, 78 couple the respective first and second runners 76, 80 to the underside of the tabletop 12. Each of the first and second runners 76, 80 extend laterally (that is from the front to the back of the table, and vice versa, along the width of the table) such that the T-coupling 66 may slide between the runners 76, 80 and the bottom of the tabletop 12 as one side of the inspection table 30 is being raised higher than the other. The bearing assembly 70 may be used to make each of the connections between the extending portion 16 of each leg and the bottom of the tabletop 12. In operation, the T-coupling 66 may sit nested within or interfacing with the top surface of the extending portion 16 such that compressive loads are transferred directly from the T-coupling 66 to the extending portion 16, rather than via the pin 68, which may be used to hold the T-coupling 66 to the extending portion 16, thereby allowing the T-coupling 66 and the extending portion 16 to rotate about each other, without the pin 68 having to pick up any compressive stress or loading. The side stopper 46 may slide up and down along the width of the inspection table 32, similar to the side stopper 46 of FIG. 1, which is aligned along the length of the inspection table 32.

In other embodiments, a plate with screws may be used to attach the extending portion 16 of each leg 14 to the tabletop 12. In other embodiments, each leg 14 may pivot on the respective wheel 20 at an interface between the leg 14 and the wheel 20, such that the linkages or couplings between the legs 14 and the tabletop 12 may be fixed even if one side of the inspection table 30 is being raised higher than the other. In one implementation of the present embodiments, the user or operator may control all four corners (that is, all four legs 14) at the same time via the control console 36, raising and lowering all four legs 14 while the tabletop 12 remains parallel to the ground. In another implementation of the present embodiments, the user or operator may control two corners (along the same length of the inspection table 30 as each other) in order to tilt the inspection table 30 for ease of viewing. In each case, the movable sides 46 and the tray locks 34 may be used in order to prevent the core trays 28 from falling off the tabletop 12.

Figure 5:
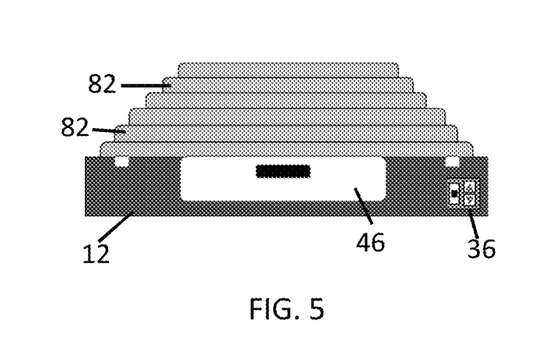
FIG. 5 illustrates a perspective view of a tabletop, according to aspects of the present embodiments.

FIG. 5 illustrates, a perspective side view of the tabletop 12, according to aspects of the present disclosed embodiments. In the embodiment of FIG. 5, the tabletop 12 includes the side stopper 46, the control console 36, as well as a plurality of rollers 82, which may be used to slide heavy core trays 28 across the top of the tabletop 12 without the operator, geoscientist, material handler, or technician needing to lift the core trays 28. The rollers 82 may be cylindrically shaped and may have a diameter from about three (3) cm to about five (5) cm, or from about 3.6 cm to about 4.0 cm. A gap of from about one (1) cm to about five (5) cm, or from about two (2) cm to about four (4) cm may be disposed between each roller 82. The rollers 82 allow the core trays 28 to be easily pushed into place during loading and unloading procedures.

Figure 6:
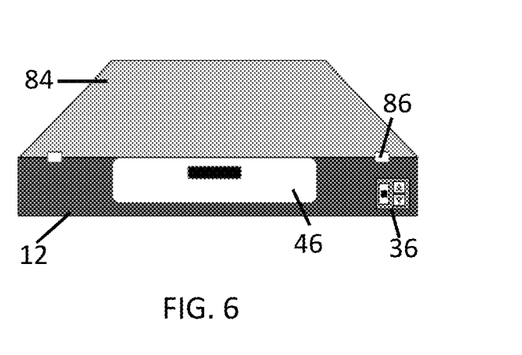
FIG. 6 illustrates a perspective view of a tabletop, according to aspects of the present embodiments.

FIG. 6 illustrates, a perspective side view of the tabletop 12, according to aspects of the present disclosed embodiments. In the embodiment of FIG. 6, the tabletop 12 includes the side stopper 46, the control console 36, a plurality of rollers 82 (not shown, disposed under the cover 84), and a cover 84 disposed on top of the rollers 82 (not shown). The cover 84 may be composed of a flexible material (or may include a flexible or malleable sheet) that is wound (and subsequently unwound from) a scroll disposed at one of the width ends of the inspection table 30. The cover 84 may be manually pulled across the rollers 82 and latched or locked into place via one or more side locks 86 disposed at one of the width ends of the inspection table 30. In other embodiments, the cover may be wound and unwound using a turning motor (not shown) coupled to the scroll. In still other embodiments, the cover 84 may be more rigid and may be placed manually over the rollers 82 such that the rigid cover 84, in connection with the rollers 82 are able to support the weight of the loaded core samples trays 28. One or more runners, guides, or grooves in the tabletop 12 (not shown) along each side length of the inspection table 30 may be used to ensure that the cover 84 remains aligned above the rollers 82. The cover 84 may be used to restrict the movement of the core trays 28 on top of the tabletop 12 such that they do not slide across the surface as easily. In one embodiment, the cover 84 may include a plurality of interlocked smaller sheets. In each of the embodiments of FIGS. 5 and 6, the side stopper 46 is in a retracted position.

Figure 7:
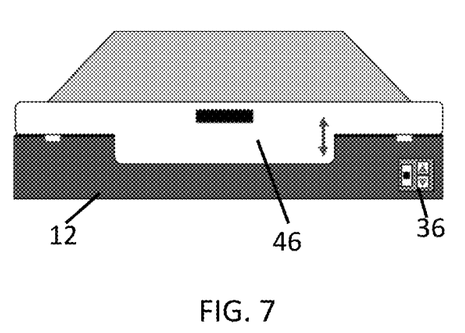
FIG. 7 illustrates a perspective view of a tabletop, according to aspects of the present embodiments.

FIG. 7 illustrates, a perspective side view of the tabletop 12 including the side stopper 46 in an extended position, as well as the control console 36.

Figure 8:
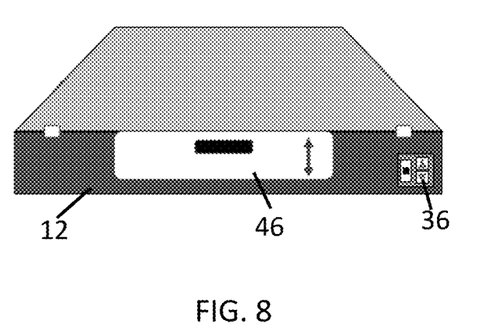
FIG. 8 illustrates a perspective view of a tabletop, according to aspects of the present embodiments.

FIG. 8 illustrates, a perspective side view of the tabletop 12 including the side stopper 46 in a retracted position, as well as the control console 36.

Core Trays

Figure 9:
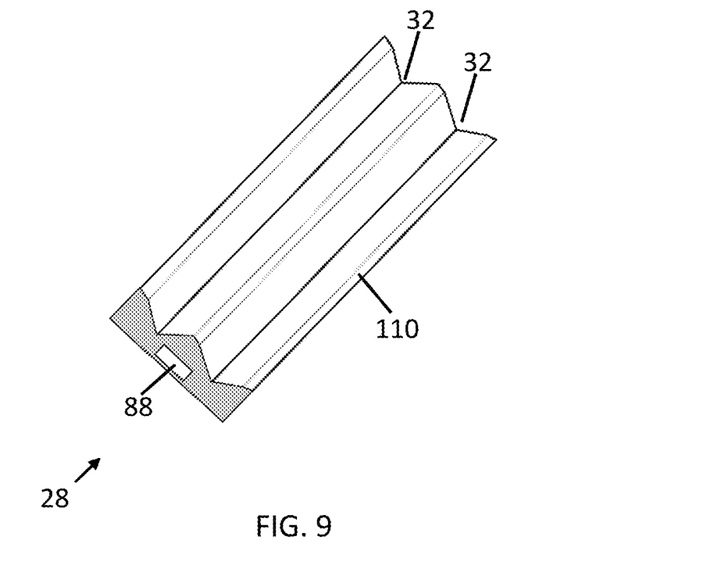
FIG. 9 illustrates a perspective view of a core tray, according to aspects of the present embodiments.

FIG. 9 illustrates a perspective view of a core tray 28 according to aspects of the present embodiments. In the embodiment of FIG. 9, the core tray 28 includes two (2) grooves 32 (or slots). In other embodiments, the core tray 28 may include three (3), four (4), five (5), six (6), seven (7) or more grooves 32 (or slots). The core tray 28 may also include one or more embedded handles 88 disposed at each width end of the core tray 28, thereby easing the carrying, moving, and general mobility of the core tray 28. The core tray 28 may also include one or more blunt edges 110, which may aid in preventing the core tray 28 from becoming damaged due to extensive handling by material handlers, technicians, operators, and geoscientists.

Figure 10:
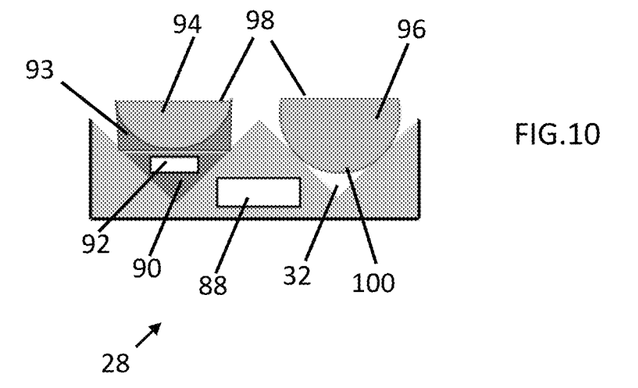
FIG. 10 illustrates a front view of a core, in accordance with aspects of the present disclosed embodiments.

FIG. 10 illustrates a front view of the core tray 28 including one or more grooves 32 (or slots) and an embedded handle 88. In the embodiment of FIG. 10, one or more core slabs including a small slab 94 and a large slab 96 are resting within the one or more grooves 32. Each of the small and large slabs 94, 96 may include a substantially flat or planar top face 98 as well as a rounded or semi-circular bottom portion 100. The small slab 94 may rest on a toblerone insert 90, which may be used to bring the top face 98 of the small slab 94 level with the top face 98 of the large slab 96. The toblerone insert 90 may include a generally triangular cross section with substantially planar sides extending longitudinally (or length-wise), and may also include one or more embedded handles 92. Stated otherwise, each toblerone insert 90 may include an elongated, triangular-prism-shaped geometry. Each toblerone insert 90 may also include one or more semi-circular sleeves 93 contoured to match the curvature of each core sample 48 or slab 94, 96. The one or more semi-circular sleeves 93 may be coupled to the top surface of the insert 90 with the contoured surface facing upward in order to receive the core sample 48 or slab 94, 96. Each core sample 48 or slab 94, 96 may rest in the semi-circular sleeve 93, thereby preventing each core sample 48 or slab 94, 96 from rolling around or rocking back and forth. Each of the small and large slabs 94, 96 may remain sitting on the sample trays 28 and may be used by inspectors, geoscientists, and technicians to inspect, examiner, transport, and archive the interior of the core slabs 48 (shown in FIG. 1). The core trays 28, as well as the one or more toblerone inserts 90 may be composed of any suitable material capable of sustaining the material stresses acting on each due to the collective weight of the core slabs 48. For example, each of the core trays 28, the semi-circular sleeves 93, and toblerone inserts 90 may be composed of polymer materials such as polyether ether ketone (PEEK), thermoplastics, composite materials including polymer matrix composites, metallic materials, galvanized stainless steel, austenitic steel, carbon steel, stainless steel, foam, fiberglass, other industrial strength materials, ceramic materials, wood, as well as other suitable materials.

Referring to FIGS. 9 and 10, each of the core trays 28 may be used to transport, inspect, clean, mark-up, and examine slabbed cores 94, 96. In addition, because each of the core slabs 94, 96 include one or more flat or planar top faces 98, multiple core trays 28 may be stacked on one another (that is, on top of the top faces 98 of each cored slab 94, 96), while the core trays 28 continue to hold the small and large slabs 94, 96. Each of the core trays 28 of FIGS. 9 and 10 may hold a length of about three (3) feet (or about one (1) meter) of core samples (slabbed or un-slabbed) thereby ensuring that the trays are of a manageable weight (for example, as compared to core trays that are sized such that they hold up to three (3) meters of core samples). As such, the core trays 28 and inspection table 10 of the present disclosed embodiments may be specifically designed to be used for multiple operations including (but not limited to) the transporting, storing, cleaning, marking, preprocessing, and examination of core samples 48 and core slabs 94, 96.

Figure 11:
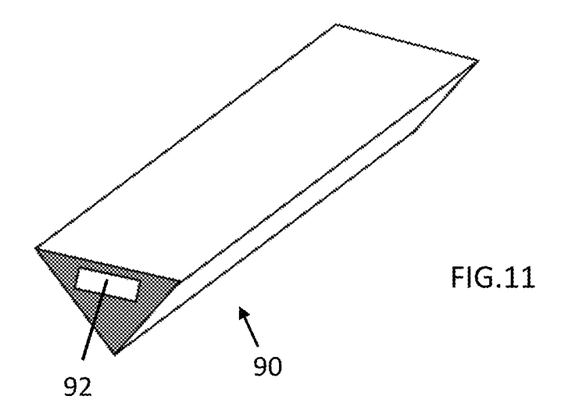
FIG. 11 illustrates a perspective view of a solid toblerone insert, according to aspects of the present embodiments.

FIG. 11 illustrates a perspective view of a solid toblerone insert 90 including an embedded handle 92.

Figure 12:
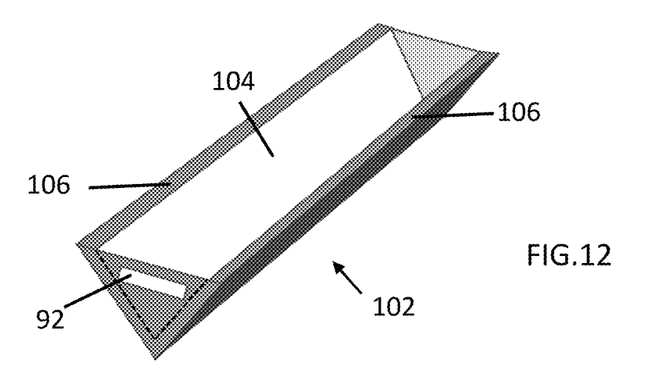
FIG. 12 illustrates a perspective view of an alternate embodiment of hollow toblerone insert, in accordance with aspects of the present disclosed embodiments.

FIG. 12 illustrates a perspective view of a hollow toblerone insert 102 including an embedded handle 92. The hollow toblerone insert 102 may include a generally hollow interior 104, and may also include one or more angled walls 106 with a thickness enabling the small core slab 94 to be elevated. In one or more embodiments, multiple hollow toblerone inserts 102 may be stacked as needed to elevate the small core slab 94 to a desired height. The hollow toblerone insert 102 may allow the small core slabs 94 to rest between the angled walls 106, thereby reducing or eliminating rocking of the small core slabs 94.

Each of the core trays 28 may be designed to fit the width of the inspection table 30 and the length of a typical core sample 48. In one embodiment, a typical core sample 48 may be up to about 100 cm in length, and the core tray 28 may be from about 100 cm to about 120 cm, or from about 100 cm to about 115 cm, or from about 102 cm to about 110 cm, to allow for spacing around the core sample 48. Each core tray 28 may be designed to handle a slabbed core with two elongated grooves 32 (which may be triangular shaped) to fit both of the slabbed cores. In another embodiment, the sample tray may include a length from about 100 cm to about 120 cm, a width from about 8 inches to about 13 inches (for example 10.43 inches), a triangular groove 32 height of 1.5 inches (or about one (1) inch to about three (3) inches), a triangular groove 32 width of four (4) inches (or about three (3) inches to about five (5) inches), and a tray base height (that is, the distance from the bottom of the core tray 28 to the bottom of the triangular groove 32) of about one (1) inch. The use of embedded handles 88 disposed within the core trays 28 (that is, as opposed to external handles) allows the core trays 28 to have a flat connection on the width side when stacked for core preparation, and also to fit within the tabletop 12 area of the inspection table 30. In one or more embodiments, multiple core trays 28 may be connected to each other on the sides using one or more locks, which may be engaged when moving the core trays 28 on rollers 82, or on the inspection tables, carts, or other equipment to secure them and prevent accidental falling of the core trays 28 and breaking of sample cores 48. The locks used for securing one or more core trays 28 may also be used to secure each core tray 28 to the inspection table 30.

The table system 10 of the present disclosed embodiments including one or more inspection tables 30 as well as core trays 28, toblerone inserts 90, and other components may be designed such that each component is robust enough to handle the heavy loads resulting from the core samples 48, while simultaneously remaining flexible, portable, and mobile enough to accommodate typical use. Industrial grade materials (such as galvanized stainless steel and others disclosed herein) may be used to ensure maximum strength while also minimizing the weight of the table system 10. Each component such as the wheels 20, bearing assembly 70, table legs 14, tabletop 12, shelf 18, as well as other components must similarly be constructed such that each may be operable given the intended use. One or more edges of the inspection table 30 may be blunted to prevent injury. For example, rubber bumpers may be disposed on corners to prevent injury and increase safety.

In operation, core preparation may involve orienting the one or more geologic core samples 48 in the core trays 28 to match one or more adjacent core samples 48. The rollers 82 disposed in the tabletop 12 may be covered via the cover 84, and the core trays 28 may be fitted parallel to the length of the inspection table 30. The movable side stoppers 46 may be deployed to prevent accidental falling of the core samples 48 or core trays 28. During core examination, the core trays 28 may be oriented parallel to the width of the inspection table 30. The rollers 82 may be used to load and unload the core trays 28. The movable side stoppers 46 may again be deployed to prevent accidental falling of the core trays 28 or core samples 48. The retractable movable tray 42 may be used to hold the equipment used in the examination process.

The present disclosed embodiments relate to core inspection tables 10 and core trays 28 specifically designed to work in conjunction with each other. The core inspection table 10 and core tray 28 system are usable in multiple scenarios including the transportation, storage, cleaning, marking, inspection, and examination of core samples 48 and core slabs 94, 96. The system may be designed to handle about three (3) feet of core samples 48 or core slabs 94, 96 per tray 28, and twelve (12) trays 28 per table 10 for a total of about thirty-six (36) feet of core samples per table 10 at any given time. As such, while held in place on the core trays 28 and inspection table 10, each core sample 48 may be: (1) cleaned, (2) aligned showing any formation dips from top right to bottom left, (3) striped with red and black lines using paint markers to indicate the top of the core samples 48 from its bottom on both sides of the core samples, (4) master orientation lined with blue color from the top of the core sample 48 to the bottom, and (5) depth marked to identify where each core sample 48 belongs. In addition, the core samples 48, slabs 94, 96, and trays 28 may be re-arranged on the table 10 from lengthwise to widthwise for ease of use during the handling process for: (1) capturing the core gamma, (2) taking 360-degree photography, (3) plugging, (4) slabbing (with the thick portion 96 and thin portion 94 laid side by side on the same tray 28), (5) etching the core with diluted acids for carbonate core, (6) core photography for capturing the slabbed surface, (7) capturing profile permeametry, and (8) special core analysis sampling, as required. All of these activities may occur while the core samples 48 stay continuously on the same tray 28 and on the same core inspection table 10, thereby minimizing the likelihood of damage, and ensuring safe handling.

The table system 10, inspection table 30, core trays 28, and other components disclosed herein emphasize safety, mobility, and versatility. The modular geologic core inspection table 30 of the present embodiments may be used in multiple scenarios including geologic core preparation by a technician to core examination by a geoscientist. The inspection table 30 and core trays 28 may be specifically designed such that they seamlessly fit together and are operable for their respective intended purposes. Each of the core trays 28 may be locked into place once properly positioned on the tabletop 12. By providing a mobile geologic core inspection table 30 and system 10 with the capability to easily transport, adjust and maneuver the inspection table 30 and contents thereof, technicians, operators, material handlers, and geoscientists may all accomplish their assigned tasked, while minimizing the likelihood of injuries.

Each of the instruments, devices, and sensors described in the present disclosure may include a wired power supply or a wireless power supply such as a battery, capacitor, or other suitable mechanism.

Elements of different implementations described may be combined to form other implementations not specifically set forth previously. Elements may be left out of the processes described without adversely affecting their operation or the operation of the system in general. Furthermore, various separate elements may be combined into one or more individual elements to perform the functions described in this specification.

Other implementations not specifically described in this specification are also within the scope of the following claims.

These and other features, aspects and advantages of the present invention will become better understood with reference to the following description and appended claims. The accompanying drawings, which are incorporated in and constitute a part of this specification, illustrate embodiments of the present disclosure and, together with the description, serve to explain the principles of the present embodiments.

Certain Definitions

In order for the present disclosure to be more readily understood, certain terms are first defined below. Additional definitions for the following terms and other terms are set forth throughout the specification.

An apparatus, composition, or method described herein as "comprising" one or more named elements or steps is open-ended, meaning that the named elements or steps are essential, but other elements or steps may be added within the scope of the composition or method. To avoid prolixity, it is also understood that any apparatus, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any apparatus, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, the term "longitudinally" generally refers to the lengthwise direction or dimension of the core inspection tables described herein.

As used herein, the term "laterally" generally refers to the widthwise direction or dimension of the core inspection tables described.

As used herein, "a" or "an" with reference to a claim feature means "one or more," or "at least one."

As used herein, the term "substantially" refers to the qualitative condition of exhibiting total or near-total extent or degree of a characteristic or property of interest.

EQUIVALENTS

It is to be understood that while the disclosure has been described in conjunction with the detailed description thereof, the foregoing description is intended to illustrate and not limit the scope of the invention(s). Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art.

What is claimed is:

1. A geologic core inspection table comprising:
   at least two legs, each leg comprising an extending portion for increasing the effective length of each leg, the extending portion at least partially concentrically disposed within or around the leg from which it extends;
   a tabletop disposed above and coupled to the at least two legs, the tabletop including a top surface for receiving a core sample tray;
   rollers disposed on the tabletop;
   a cover covering the rollers; and
   a side stopper for preventing core samples from falling off the geologic core inspection table,
   where at least one leg is extended to a different height than at least one other leg.

2. The table of claim 1, where each extending portion is telescopically coupled to the respective leg from which it extends.

3. The table of claim 1, where the top surface for receiving the core sample tray is oriented at an angle from about 10 degrees to about 30 degrees relative to a horizontal direction.

4. The table of claim 3, further comprising a bearing assembly coupling at least one of the legs to a bottom surface of the tabletop.

5. The table of claim 4, where the bearing assembly comprises a T-coupling.

6. The table of claim 5, further comprising:
   a retractable movable tray coupled to a bottom surface of the tabletop;
   a control console disposed on the tabletop; and
   a shelf coupled to the legs and disposed beneath the tabletop.

7. The table of claim 6, further comprising:
   wheels coupled to the legs;
   a brake coupled to one of the wheels; and
   a manual brake release coupled to the brake,
   where the wheels comprise a castor, and
   where each extending portion is telescopically coupled to the leg from which it extends.

8. The table of claim 1, further comprising a retractable movable tray coupled to a bottom surface of the tabletop.

9. The table of claim 1, further comprising a control console disposed on the tabletop, the control console controlling the height of the tabletop.

10. The table of claim 1, further comprising a shelf coupled to the at least two legs and disposed beneath the tabletop.

11. The table of claim 1, further comprising a hydraulic system comprising:
    a pneumatic cylinder disposed within a hollow interior of a leg;
    hydraulic fluid disposed within the pneumatic cylinder; and
    a hydraulic fluid pressure source fluidly connected to the hydraulic fluid.

12. A geologic core inspection table comprising:
    at least three legs, each leg comprising a wheel coupled thereto, the wheels allowing movement of the table in both a lateral direction and a longitudinal direction;
    a tabletop disposed above and coupled to the at least three legs, the tabletop including a top surface for receiving a core sample tray;
    rollers disposed on the tabletop;
    a cover covering the rollers; and
    a side stopper for preventing core samples from falling off the geologic core inspection table,
    where at least one leg is extended to a different height than at least one other leg.

13. The table of claim 12, further comprising a brake coupled to the wheel, the brake comprising a spring for engaging the brake on the wheel.

14. The table of claim 13, further comprising a manual brake release coupled to the brake.

15. The table of claim 12, where the wheel comprises a castor.

16. A geologic core inspection table system comprising:
    a core tray for holding core samples, the core tray comprising two or more grooves disposed therein, each groove of the two or more grooves extending longitudinally for receiving a core sample; and
    a geologic core inspection table comprising:
      at least two legs;
      a tabletop disposed above and coupled to the legs, the tabletop including a surface for receiving the core tray;
      rollers disposed on the tabletop;
      a cover covering the rollers; and
      a side stopper for preventing core samples from falling off the geologic core inspection table,
      where at least one leg is extended to a different height than at least one other leg.

17. The system of claim 16, where the core tray has a length from about 100 cm to about 120 cm.

18. The system of claim 16, further comprising a toblerone insert disposed within a groove, wherein the toblerone insert comprises a generally triangular cross section such that the toblerone insert sits inside the groove.

19. The system of claim 18, where the toblerone insert and the core tray each comprise at least one embedded handle.

20. The system of claim 16, where at least one of the core tray and the geologic core inspection table is composed of austenitic steel, carbon steel, galvanized stainless steel, titanium, or a combination thereof.

21. The system of claim 16, where the geologic core inspection table comprises at least four legs.

22. The system of claim 16, where at least two legs comprise a bottom portion extending parallel to the ground.

23. The system of claim 22, where the at least two legs comprise an upside-down "T" shape or an "I" shape.

24. The table of claim 1, where the top surface for receiving a core sample tray is oriented at an angle from about 5 degrees to about 35 degrees relative to a surface on which the geologic core inspection table is resting.

25. The table of claim 1, further comprising a control console disposed on the tabletop, the control console controlling the height of the tabletop relative to a surface on which the geologic core inspection table is resting.

* * * * *